(12) United States Patent
Grunenberg et al.

(10) Patent No.: US 9,637,459 B2
(45) Date of Patent: May 2, 2017

(54) SODIUM AND CALCIUM SALTS OF DIHYDROQUINAZOLINE DERIVATIVE AND USE THEREOF AS ANTIVIRAL AGENTS

(71) Applicant: AiCuris GmbH & Co. KG, Wuppertal (DE)

(72) Inventors: Alfons Grunenberg, Wuppertal (DE); Mathias Berwe, Sprockhovel (DE); Birgit Keil, Dusseldorf (DE); Edwin Aret, CJ Almere (NL); Kerstin Paulus, Ratingen (DE); Wilfried Schwab, Velbert (DE)

(73) Assignee: AICURIS GMBH & CO KG., Wuppertal (DE)

( * ) Notice: Subject to any disclaimer, the term of this patent is extended or adjusted under 35 U.S.C. 154(b) by 0 days.

(21) Appl. No.: 14/381,618

(22) PCT Filed: Feb. 28, 2013

(86) PCT No.: PCT/EP2013/054115
§ 371 (c)(1),
(2) Date: Aug. 28, 2014

(87) PCT Pub. No.: WO2013/127971
PCT Pub. Date: Sep. 6, 2013

(65) Prior Publication Data
US 2015/0038514 A1    Feb. 5, 2015

(30) Foreign Application Priority Data
Feb. 29, 2012 (DE) .................. 10 2012 101 659

(51) Int. Cl.
*C07D 239/74* (2006.01)
*C07D 239/84* (2006.01)

(52) U.S. Cl.
CPC ......... *C07D 239/74* (2013.01); *C07D 239/84* (2013.01)

(58) Field of Classification Search
CPC ..................................... C07D 239/84
See application file for complete search history.

(56) References Cited

U.S. PATENT DOCUMENTS

| 7,196,086 B2 | 3/2007 | Wunberg et al. |
| 8,513,255 B2 | 8/2013 | Wunberg et al. |
| 2005/0065160 A1 | 3/2005 | Wunberg et al. |
| 2007/0191387 A1 | 8/2007 | Wunberg et al. |

FOREIGN PATENT DOCUMENTS

| WO | 2004/096778 A1 | 11/2004 | |
| WO | WO2004/096778 | * 11/2004 | ........... C07D 239/84 |

OTHER PUBLICATIONS

International Search Report dated May 31, 2013 issued in corresponding PCT/EP2013/054115 application (pp. 1-2).

* cited by examiner

*Primary Examiner* — Paul V Ward
(74) *Attorney, Agent, or Firm* — Millen White Zelano and Branigan, PC; Csaba Henter; Anthony Zelano

(57) ABSTRACT

The invention relates to sodium and calcium salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid and solvates thereof, to the use thereof in a method of treatment and/or prophylaxis of virus infections and to the use thereof for producing drugs for use in methods of treatment and/or prophylaxis of diseases, more particularly the use thereof as antiviral agents, more particularly against cytomegaloviruses.

20 Claims, 5 Drawing Sheets

Fig. 5:

| | RT | RRT | Peak height (µAU) | Code | Area (µV*sec) | FKF | Norm% | Denomination | Reported individual value |
|---|---|---|---|---|---|---|---|---|---|
| 1 | 26.986 | 1.00 | 538852 | BB | 9219786 | 1.00 | 99.9093 | sodium salt | 99.9093 |
| 2 | 29.050 | | | Missing | | | | Di-p-toluoyl-tartaric acid | |
| 3 | 29.640 | 1.10 | 427 | BB | 8373 | | 0.0907 | | 0.0907 |
| 4 | 33.407 | | | Missing | | | | quinazolylpiperazine | |
| 5 | 36.932 | | | Missing | | | | quinazolinethylester | |
| 6 | 41.822 | | | Missing | | | | quinazolylidipiperazine | |
| Sum | | | | | | | 100.0000 | | |

# SODIUM AND CALCIUM SALTS OF DIHYDROQUINAZOLINE DERIVATIVE AND USE THEREOF AS ANTIVIRAL AGENTS

The present invention relates to salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid and solvates thereof.

The invention further relates to methods for their production, their use in methods of treatment and/or prevention of diseases, in particular of virus infections, as well as their use for the production of drugs for use in methods of treating and/or preventing virus infections, in particular for use in methods of treating and/or preventing infections with human cytomegaloviruses (HCMV) or another representative of the Herpes viridae group.

{8-fluoro-2-[4-(3-methoxyphenyl)piperazine-1-yl]-3-[2-methoxy-5-(trifluoromethyl)phenyl]-3,4-dihydroquinazoline-4-yl}acetic acid is known, for example, from WO 2004/096778, full disclosure of which is included herein by reference; it was developed by Applicant as a promising candidate for an antivirally active substance, in particular for combating infections caused by the human cytomegalovirus (HCMV). In the development process it has, however, proven extremely complicated to obtain the compound in crystalline form, whether as a zwitterion or in the form of a salt, and until now development has been carried out using the zwitterion in amorphous form. However, the use of amorphous substances to produce drugs is undesirable because, on the one hand, it is often difficult to guarantee uniform purity with amorphous substances, and on the other hand, it is also difficult to guarantee uniform pharmacological parameters with amorphous substances, such as uniform bioavailability.

It is therefore an object of the invention to describe salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid with which crystalline products can be obtained. In order for it to be reasonably possible to use the salts for the development of drugs, they must also remain stable in storage over a long period of time. Finally, the crystalline compounds must also be readily soluble in an aqueous medium and particularly at physiological pH.

In addition, the salts according to the invention possess a high degree of purity.

In the context of the present invention the term "crystalline product" denotes S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid sodium salts and S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid calcium salts which, under X-ray diffraction analysis, possess the characteristic peak pattern as shown in the relevant FIGS. 1-3, or a similar peak pattern.

In the context of the invention, the term "storage-stable" means, in the case of the salts according to the invention, that at 25° C. they contain a minimum proportion of >90%, preferably >95%, and most preferably 99% of {8-fluoro-2-[4-(3-methoxyphenyl)piperazine-1-yl]-3-[2-methoxy-5-(trifluoromethyl)phenyl]-3,4-dihydroquinazoline-4-yl}acetic acid for a storage period of at least two, preferably at least three, even more preferably at least six weeks, and most preferred 12 months, when said salts are measured using one of the HPLC methods 1-3. Said storage stability of the salts is regarded as adequate within the scope of the invention.

Surprisingly, it has now been discovered that {8-fluoro-2-[4-(3-methoxyphenyl)piperazine-1-yl]-3-[2-methoxy-5-(trifluoromethyl)phenyl]-3,4-dihydroquinazoline-4-yl}acetic acid forms well-define crystalline salts with sodium and calcium cations. It has further been discovered that these salts are readily soluble and also exhibit good storage stability in an aqueous medium, in particular at physiological pH.

Furthermore, the crystalline sodium and calcium salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid which are obtained according to the invention exhibit a high degree of purity.

The terms "high purity, purity and pure" when used in connection with the S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid sodium salts and the S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid calcium salts according to the invention denote its presence as a substance in a mixture of substances with a <0.1%, preferably <0.08%, more preferably 0.05%, and most preferred <0.01% total proportion of its known impurities Di-p-toluoyl-D-tartaric acid, and/or S-quinazolyl-piperazine, and/or quinazoline ethyl ester, and/or quinazolyl-dipiperazine, and/or its non-specific impurities, when measured by means of HPLC according to exemplary embodiment F).

Thus, subject matter of the invention are the crystalline sodium salts and crystalline calcium salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, as well as their solvates.

Within the scope of the invention, sodium and calcium salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid are adducts of a reaction of {8-fluoro-2-[4-(3-methoxyphenyl)piperazine-1-yl]-3-[2-methoxy-5-(trifluoromethyl)phenyl]-3,4-dihydroquinazoline-4-yl}acetic acid with strong sodium or calcium bases, in particular sodium hydroxide or calcium hydroxide. The {8-fluoro-2-[4-(3-methoxyphenyl)piperazine-1-yl]-3-[2-methoxy-5-(trifluoromethyl)phenyl]-3,4-dihydroquinazoline-4-yl}acetic acid and the sodium or calcium counterions may be present in any ratio. A whole number ratio (e.g. 1:1, 1:2, 1:3, 3:1, 2:1) is preferred. The salts may be produced by a direct reaction of the {8-fluoro-2-[4-(3-methoxyphenyl)piperazine-1-yl]-3-[2-methoxy-5-(trifluoromethyl)phenyl]-3,4-dihydroquinazoline-4-yl}acetic acid with sodium or calcium bases or by producing another basic salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid followed by replacement of the counterion.

Within the scope of the invention the term "solvates" refers to those forms of the salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid which form a complex through coordination with solvent molecules. Hydrates are a special form of solvates in which the coordination takes place with water.

Within the scope of the present invention preferred is the monocalcium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, in particular the 2,5-hydrate and the 3,5-hydrate of the monocalcium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid. Furthermore, within the scope of the invention, the monosodium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid is preferred and in particular the 3-hydrate of the monosodium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid.

In addition, within the scope of the invention, preferred is a 2,5-hydrate of the monocalcium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid which exhibits characteristic peaks at about 6.1, 9.2 and 15.5 degrees 2theta in the X-ray powder diffractogram (XRD).

In addition, within the scope of the invention, preferred is a 3,5-hydrate of the monocalcium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid which exhibits characteristic peaks at about 6.2, 12.4 and 22.4 degrees 2theta in the X-ray powder diffractogram (XRD).

Also preferred within the scope of the invention is a 3-hydrate of the monosodium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid which exhibits characteristic peaks at about 6.2, 20.9 and 22.4 degrees 2theta in the X-ray powder diffractogram (XRD).

As is readily apparent to a person skilled in the art, {8-fluoro-2-[4-(3-methoxyphenyl)piperazine-1-yl]-3-[2-methoxy-5-(trifluoromethyl)phenyl]-3,4-dihydroquinazoline-4-yl}acetic acid possesses a stereocentre at the carbon in the 4-position in the dihydroquinazoline ring. Within the scope of the present invention, it is particularly preferred that this carbon possesses the S-configuration.

The salts according to the invention are in general produced by reacting {8-fluoro-2-[4-(3-methoxyphenyl)piperazine-1-yl]-3-[2-methoxy-5-(trifluoromethyl)phenyl]-3,4-dihydroquinazoline-4-yl}acetic acid or an acid salt thereof with a sodium or calcium base, in particular sodium hydroxide or calcium hydroxide, in a solvent.

It is in addition possible to react a base salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, which is not a sodium or calcium salt, with a source for sodium or calcium cations in a solvent.

For the aforementioned reactions, in particular a mixture of at least one di-($C_1$-$C_4$)-alkyl ether and at least one ($C_1$-$C_4$)-alcohol is used as the solvent.

Thus, subject matter of the invention is also a method to produce a sodium or calcium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid using the following steps:

a.) Dissolve {8-fluoro-2-[4-(3-methoxyphenyl)piperazine-1-yl]-3-[2-methoxy-5-(trifluoromethyl)phenyl]-3,4-dihydroquinazoline-4-yl}-acetic acid or a solvate thereof in a mixture of at least one di-($C_1$-$C_4$)-alkyl ether and at least one ($C_1$-$C_4$)-alcohol, if necessary under heat.

b.) Add NaOH or Ca(OH)$_2$ to the solution obtained in step a.), c.) Remove a portion of the solvent from the solution obtained in step b.) and inoculate, if necessary, with suitable seed crystals in order to initiate the crystallization of the salt or of a solvate of the salt, d.) Separate the crystallized-out salt or solvate thereof obtained in step c.), e.) If necessary, stir the salt or solvate obtained in step d.) in a suitable solvent, preferably in a mixture of water and at least one ($C_1$-$C_4$)-alcohol in order to obtain a desired solvate, and f.) Dry the salt or solvate obtained in step d.) or e.).

The salts according to the invention that are obtained in this way can, if necessary, be further processed, e.g. recrystallized or micronized, in order to further adapt their physical properties to the intended purpose.

The {8-fluoro-2-[4-(3-methoxyphenyl)piperazine-1-yl]-3-[2-methoxy-5-(trifluoromethyl)phenyl]-3,4-dihydroquinazoline-4-yl}acetic acid, which is used to produce the salts according to the invention, is known and can be produced, for example, by the method described in WO 2006/133822.

The production takes place in particular by the saponification of the ester of a compound having the formula (II)

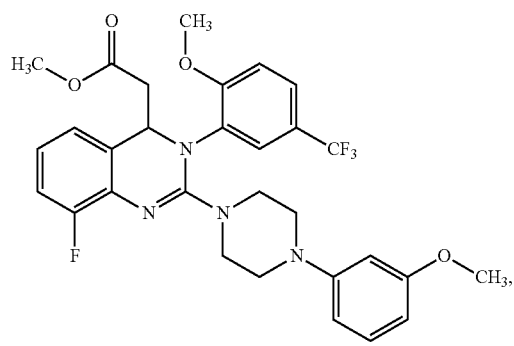

(II)

with a base.

The compound having the formula (II) can be produced by reacting a compound having the formula (III)

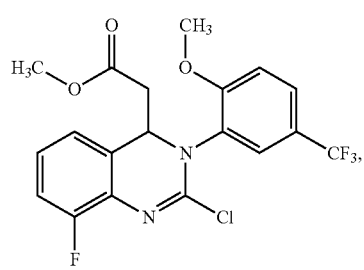

(III)

with a compound having the formula (IV) in the presence of a base

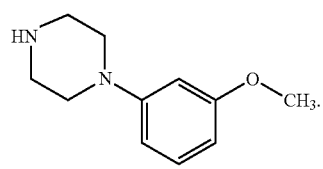

(IV)

The compound having the formula (III) can be produced by reacting a compound having the formula (V)

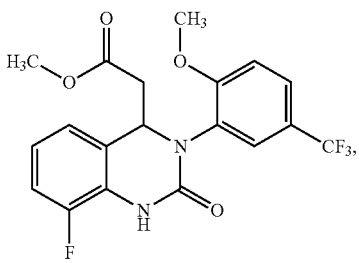

with phosphorus oxychloride, phosphorus trichloride or phosphorus pentachloride in the presence of a base.

The compound having the formula (V) can be produced by reacting a compound having the formula (VI)

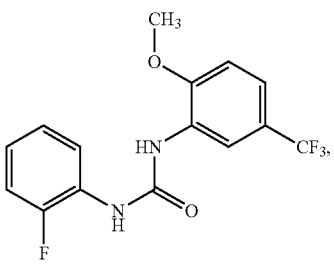

in the first step with acrylic acid method ester in the presence of a palladium catalyst and oleum, and in the second step with a base.

Compounds having the formulae (IV) and (VI) are in principle known to a person skilled in the art or can be produced by customary methods known from the literature.

The saponification of the ester of a compound having the formula (II) to form {8-fluoro-2-[4-(3-methoxyphenyl)piperazine-1-yl]-3-[2-methoxy-5-(trifluoromethyl)phenyl]-3,4-dihydroquinazoline-4-yl}acetic acid is achieved by reacting a compound having the formula (II) with a base in an inert solvent, in a temperature range from 18° C. up to reflux of the solvent, preferably at 18 to 50° C., more preferred at 20 to 30° C., at normal pressure, within a period of, for example, 0.5 to 10 hours, preferably within 1 to 5 hours.

Bases are, for example, alkali hydroxides, such as sodium, lithium or potassium hydroxide, or alkali carbonates, such as cesium carbonate, sodium or potassium carbonate, or alcoholates such as sodium or potassium methanolate, or sodium or potassium ethanolate, where the base may be present in aqueous solution.

Inert solvents are, for example, ethers, such as 1,2-dimethoxyethane, methyl tert-butyl ether (MTBE), dioxane, tetrahydrofuran, glycol dimethyl ether or diethylene glycol dimethyl ether, alcohols such as methanol, ethanol, n-propanol, iso-propanol, n-butanol or tert-butanol, or water, or mixtures of solvents.

Sodium hydroxide in water and MTBE are preferred.

The synthesis of a compound having the formula (II) from a compound having the formula (III) and a compound having the formula (IV), in the presence of a base, takes place in an inert solvent, in a temperature range from 40° C. up to reflux of the solvent, preferably at reflux of the solvent, at normal pressure, within for example 2 to 48 hours, preferably within 4 to 12 hours.

Bases are, for example, amine bases such as 1,8-diazabicyclo[5.4.0]undec-7-ene (DBU), 1-(3-methoxyphenyl)piperazine or triethylamine, or other bases such as potassium tert-butylate.

Inert solvents are, for example, chlorobenzene or ethers such as 1,2 dimethoxyethane, dioxane, glycol dimethyl ether or diethylene glycol dimethyl ether.

DBU in dioxane is preferred.

The conversion of a compound having the formula (V) to a compound having the formula (III) takes place by reacting a compound having the formula (V) with phosphorus oxychloride, phosphorus trichloride or phosphorus pentachloride, with phosphorus oxychloride being preferred, in the presence of a base in an inert solvent, in a temperature range from 40° C. up to reflux of the solvent, preferably at reflux of the solvent, at normal pressure, within for example 1 to 48 hours, preferably within 2 to 12 hours.

Bases are, for example, amines such as 1,8-diazabicyclo[5.4.0]undec-7-ene (DBU), pyridine or triethylamine, or other bases such as potassium tert-butylate.

Inert solvents are for example hydrocarbons such as benzene, xylene, toluene or chlorobenzene.

DBU in chlorobenzene is preferred.

The conversion of a compound having the formula (VI) to a compound having the formula (V) takes place, in the first step, by reacting a compound of the formula (VI) with acrylic acid methyl ester in the presence of a palladium catalyst and oleum in a solvent, in a temperature range from 0° C. to 40° C., preferably at room temperature, and in the second step by reaction with a base in an inert solvent, in a temperature range from 40° C. up to reflux of the solvent, preferably at reflux of the solvent, at normal pressure, within for example 1 to 48 hours, preferably within 2 to 12 hours.

Palladium catalysts in the first step are, for example, palladium(II) acetate, bis(triphenylphosphine)palladium(II) chloride, tetrakis(triphenylphosphine)palladium(0), bis(tri (o-tolyl)phosphine)palladium-(II)-chloride, or a palladium catalyst produced from bis(acetonitrile)dichloropalladium or palladium(II) acetate and a ligand, for example tris(o-tolyl)phosphine, triphenylphosphine or diphenylphosphino ferrocene.

Solvents in the first step are, for example, organic acids such as acetic acid or propionic acid.

Palladium(II) acetate in acetic acid is preferred.

Bases in the second step are, for example, DBU, triethylamine or diisopropylethylamine.

Inert solvents in the second step are, for example, ethers such as 1,2-dimethoxyethane, dioxane, glycol dimethyl ether or diethylene glycol dimethyl ether, hydrocarbons such as benzene, xylene or toluene, or other solvents such as isobutyronitrile, acetonitrile, acetone, nitrobenzene, dimethylformamide, dimethylacetamide, dimethylsulfoxide or N-methylpyrrolidone.

DBU in acetone is preferred.

The production of the {8-fluoro-2-[4-(3-methoxyphenyl)piperazine-1-yl]-3-[2-methoxy-5-(trifluoromethyl)phenyl]-3,4-dihydroquinazoline-4-yl}acetic acid used to produce the salts according to the invention is described in more detail, by way of example, in the following Synthesis Diagram 1. This synthesis diagram is nothing more than an example and should in no way be understood as restrictive.

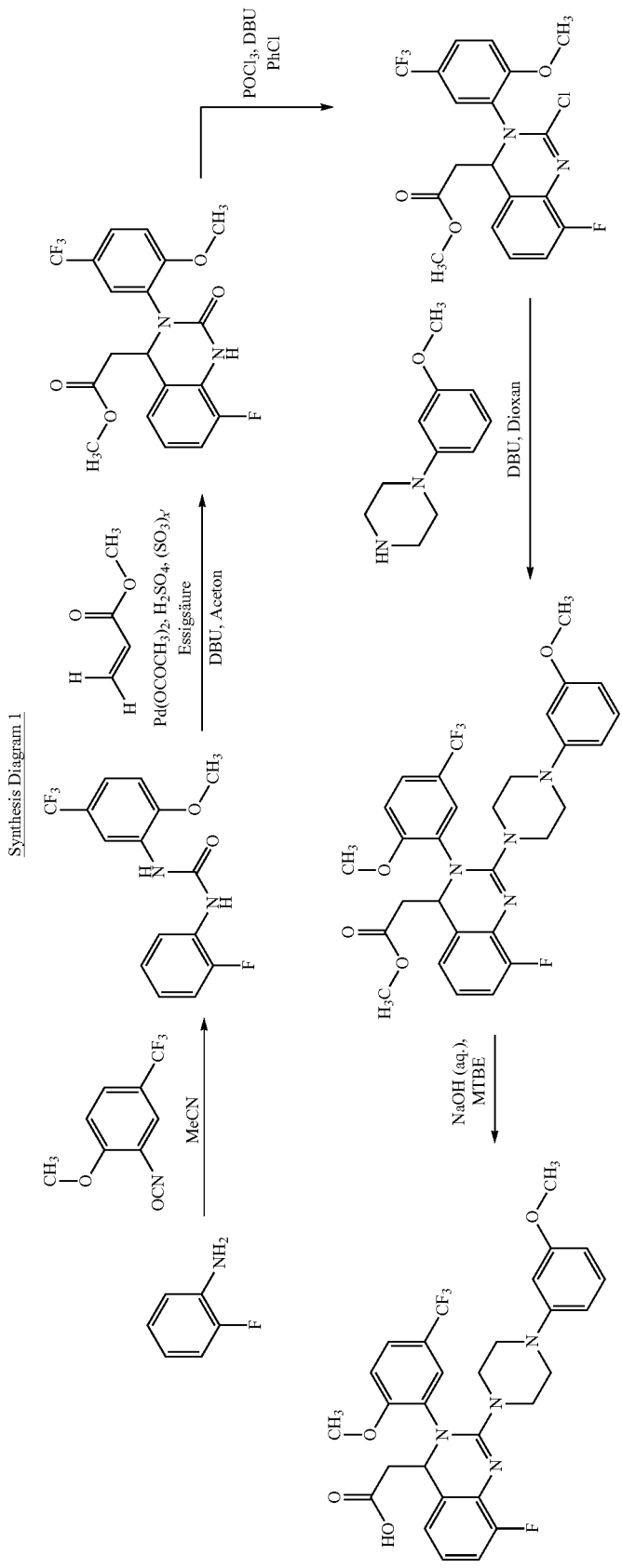
Synthesis Diagram 1

[Translation key: Essigsäure=acetic acid]

As already mentioned above, the {8-fluoro-2-[4-(3-methoxyphenyl)piperazine-1-yl]-3-[2-methoxy-5-(trifluoromethyl)phenyl]-3,4-dihydroquinazoline-4-yl}acetic acid is used preferably in the form of the S-enantiomer. This S-enantiomer can be produced as shown, for example, in the following Synthesis Diagram 2.

The following areas of indication can be mentioned, by way of example:
1) Treatment and prevention of HCMV infections in AIDS patients (retinitis, pneumonitis, gastrointestinal infections).
2) Treatment and prevention of cytomegalovirus infections in bone marrow and organ transplant patients who often contract life-threatening HCMV pneumonitis or encephalitis, as well as gastrointestinal and systemic HCMV infections.
3) Treatment and prevention of HCMV infections in neonates and infants.
4) Treatment of acute HCMV infection in pregnant women.
5) Treatment of HCMV infection in immune-suppressed patients suffering from cancer and undergoing cancer therapy.
6) Treatment of HCMV-positive cancer patients with the aim of reducing HCMV-mediated tumour progression (cf. J. Cinatl, et al., FEMS Microbiology Reviews 2004, 28, 59-77).

Synthesis Diagram 2

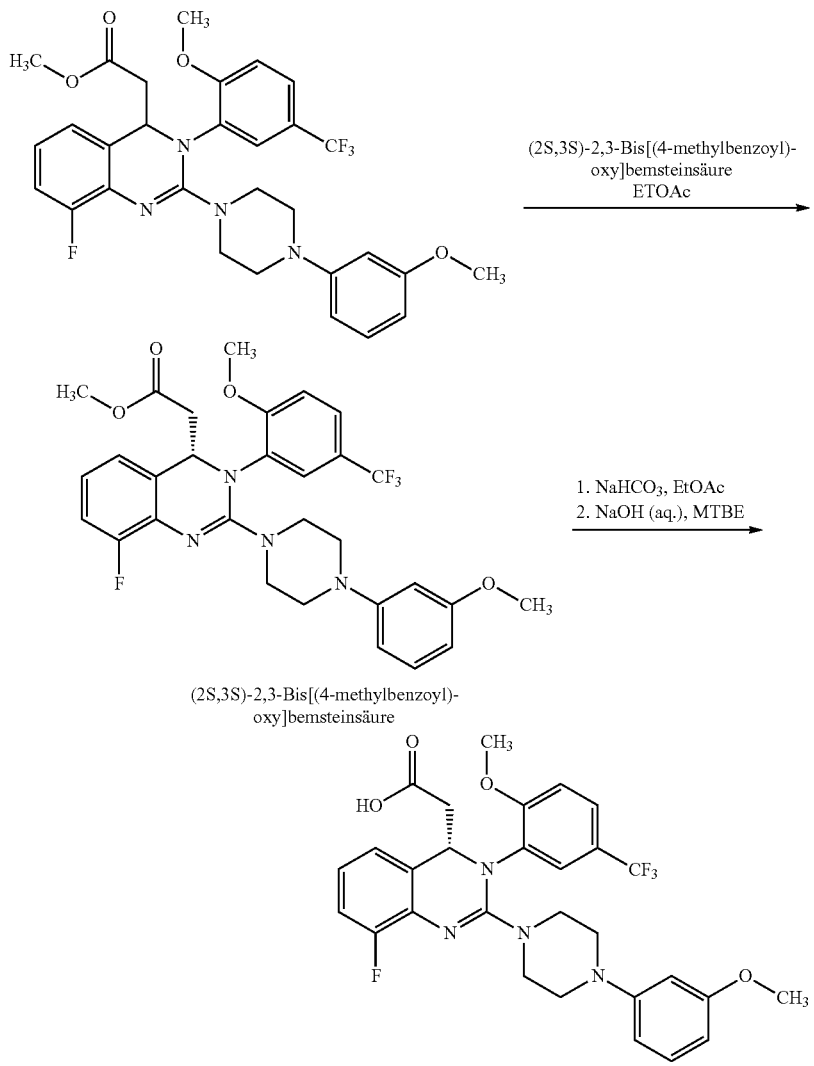

[Translation key: Bernsteinsäure=succinic acid]

The salts according to the invention exhibit an antiviral effect against representatives of the Herpes viridae group (herpes viruses), above all against the cytomegaloviruses (CMV), in particular against the human cytomegalovirus (HCMV). They are thus suitable for use in methods of treating and preventing diseases, especially infections with viruses, in particular the viruses referred to herein and the infectious diseases caused by them. The term "virus infection" is understood here to mean not only an infection with a virus but also a disease caused by infection with a virus.

Due to their properties and characteristics the salts according to the invention can be used to produce drugs that are suitable for use in methods of preventing and/or treating diseases, in particular virus infections.

The salts according to the invention are preferably used to produce drugs which are suitable for use in prevention and/or treating infections with a representative of the Herpes viridae group, in particular a cytomegalovirus, in particular the human cytomegalovirus.

Due to their pharmacological properties and characteristics, the salts according to the invention can be used by themselves and, if needed, also in combination with other active substances, especially antiviral substances such as for example valganciclovir, ganciclovir, valacyclovir, acyclovir, foscarnet, cidofovir and related derivatives in methods of treating and/or preventing virus infections, in particular HCMV infections.

Further subject matter of the present invention is the use of the salts according to the invention in a method of treating and/or preventing diseases, preferably virus infections, in particular infections with the human cytomegalovirus (HCMV) or another representative of the Herpes viridae group.

Further subject matter of the present invention is the use of the salts according to the invention in methods of treating and/or preventing diseases, in particular the aforementioned diseases.

Further subject matter of the present invention is the use of the salts according to the invention to produce a drug for use in treating and/or preventing diseases, in particular the aforementioned diseases.

Further subject matter of the present invention is the use in a method for treating and/or preventing diseases, in particular the aforementioned disease, by using an antivirally effective amount of the salts according to the invention.

The salts according to the invention may be effective systemically and/or locally. For this purpose they can be applied in a suitable manner, e.g. by the oral, parenteral, pulmonal, nasal, sublingual, lingual, buccal, rectal, dermal, transdermal, conjunctival, or otic route, or as an implant or stent.

The salts according to the invention can be administered in suitable forms for these drug administration routes.

Means of administration that function according to the state of the art and that release the salts according to the invention quickly and/or in modified form are suitable for oral administration; said means of administration contain the compounds according to the invention in crystalline and/or amorphized and/or dissolved form, e.g. tablets (non-coated or coated tablets, for example enteric-coated or with coatings that dissolve slowly or are insoluble, which control the release of the compound according to the invention), tablets or film-coated/wafer-like forms that dissolve quickly in the mouth, film-coated forms/lyophilisates, capsules (for example hard or soft gelatin capsules), sugar-coated tablets, granulates, pellets, powder, emulsions, suspensions, aerosols or solutions.

Parenteral administration can take place by avoiding a resorption step (e.g. intravenous, intra-arterial, intracardiac, intraspinal, or intralumbar administration) or by making use of resorption (e.g., intramuscular, subcutaneous, intracutaneous, percutaneous or intraperitoneal administration). For parenteral administration, suitable means include injection and infusion preparations in form of solutions, suspensions, emulsions, lyophilisates or sterile powders.

The following means are suitable for the other routes of administration, for example inhalation drugs (e.g. powder inhalers, nebulizers), nose drops, nose solutions, nose sprays; tablets, film-coated/wafer-like medications, or capsules for lingual, sublingual or buccal administration, suppositories, ear or eye preparations, vaginal capsules, aqueous suspensions (lotions, shake mixtures), lipophilic suspensions, ointments, creams, transdermal therapeutic systems, milk, pastes, foams, dusting powder, implants or stents).

The salts according to the invention can be converted into the above-mentioned forms of administration. This can be done in a known manner by mixing with inert, non-toxic, pharmaceutically suitable excipients. The latter include carrier substances (e.g. microcrystalline cellulose, lactose, mannitol), solvents (e.g. liquid polyethylene glycols), emulsifiers and dispersants or wetting agents (for example sodium dodecyl sulfate, polyoxysorbitan oleate), binding agents (e.g. polyvinylpyrrolidone), synthetic and natural polymers (e.g. albumin), stabilizers (e.g. antioxidants such as ascorbic acid), dyes (e.g. inorganic pigments such as iron oxides) and flavour and/or odour correctors.

Further subject matter of the present invention are drugs which contain at least one salt according to the invention, usually together with one or more inert, non-toxic, pharmaceutically suitable excipients, as well as the use thereof for the aforementioned purposes.

In general, to achieve effective results in intravenous administration, it has been found advantageous to administer quantities, in terms of the pure substance, of about 0.001 to 10 mg/kg, preferably about 0.01 to 5 mg/kg body weight. In the case of oral administration, the dosage is usually about 0.01 to 25 mg/kg, preferably about 0.1 to 10 mg/kg of body weight.

Nonetheless it can sometimes be necessary to deviate from said quantities, namely depending on body weight, administration route, individual response to the active substance, nature of the preparation and time or interval at which the administration takes place. For example, in certain cases it may be sufficient to get by with less than the aforementioned minimum amount, while in other cases the stated upper limit has to be exceeded. When administering large amounts it may be recommendable to distribute these in several individual doses over the course of a day.

It is understood that the features referenced above and to be explained below can be used not only in the combination respectively given, but also in other combinations or alone without departing from the scope of the present invention.

The invention will now be described in more detail on the basis of examples, as well as with reference to the attached drawings, which show:

BRIEF DESCRIPTION OF THE FIGURES

FIG. 5 Analysis of an HPLC-chromatogram according to FIG. 4 in tabular form.

Figure 1:
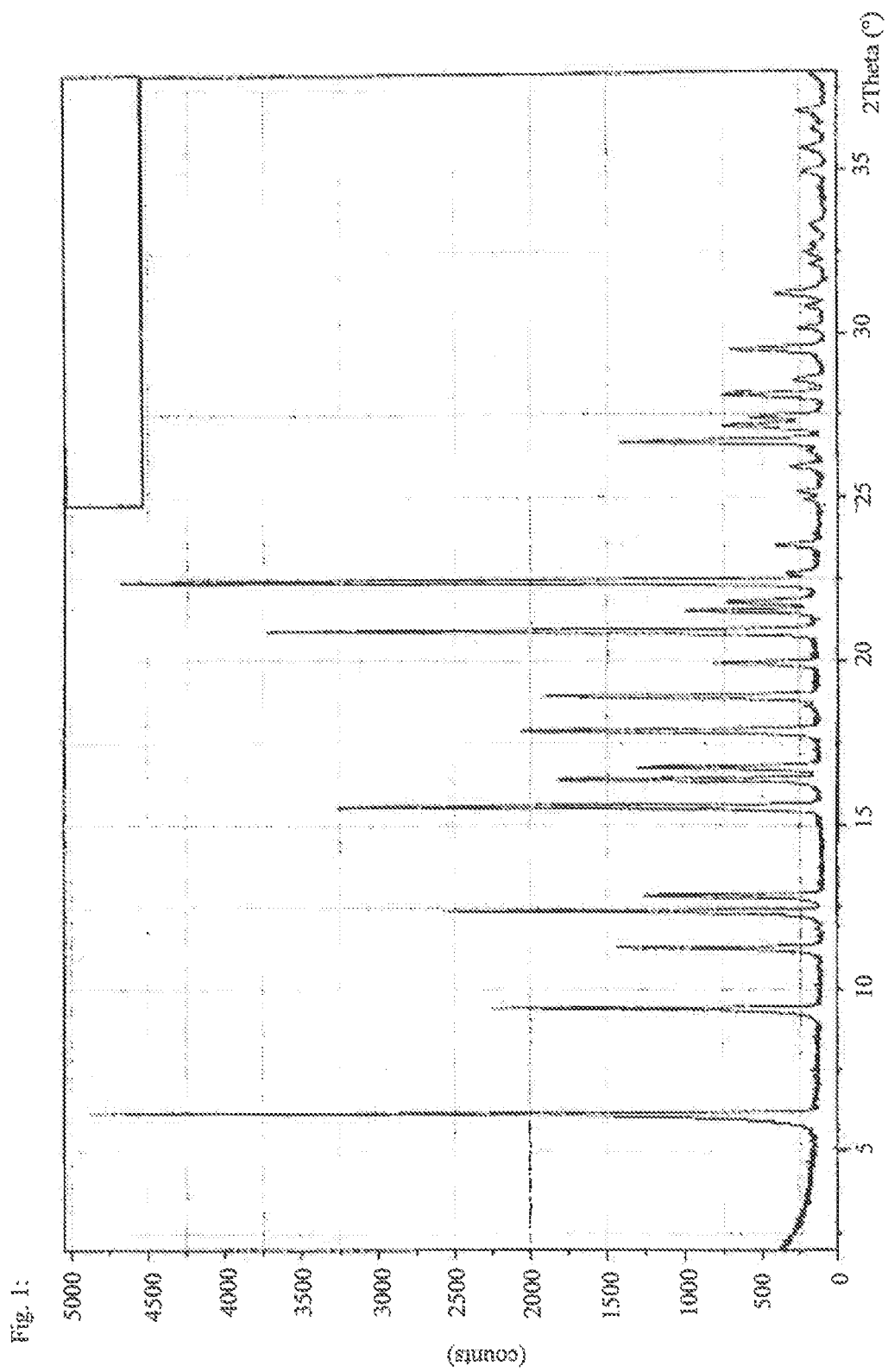
FIG. 1 an X-ray powder diffractogram (XRD) of a 3-hydrate of the sodium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid that was produced according to Example 2.

Unless indicated otherwise, the percentages given in the following tests and examples are weight percentages, parts are weight proportions. Solvent ratios, dilution ratios and concentrations of liquid solutions relate, in each case, to the volume.

List of Abbreviations
ACN Acetonitrile
API active pharmaceutical ingredient
API-ES-pos. Atmospheric pressure ionization, electrospray, positive (in MS)
API-ES-neg. Atmospheric pressure ionization, electrospray, negative (in MS)
ca. circa
CI, $NH_3$ chemical ionization (with ammonia)
DBU 1,8-Diazabicyclo[5.4.0]undec-7-en
DMAP 4-(Dimethylamino)pyridine
DMSO Dimethyl sulfoxide
ESTD external standardization
h hour(s)
HPLC high pressure liquid chromatography
conc. concentrated
min. minutes
MS mass spectroscopy
MTBE Methyl tert-butylether
NMR nuclear magnetic resonance spectroscopy
$R_T$ retention time (in HPLC)
VTS vacuum drying cabinet General HPLC Methods Method 1 (HPLC): Instrument: HP 1050 with variable wavelength detection; column: Phenomenex Prodigy ODS (3) 100A, 150 mm×3 mm, 3 µm; Eluent A: (1.0 g KH2PO4+ 1.0 ml H3PO4)/l water, Eluent B: acetonitrile; gradient: 0 min 10% B, 25 min 80% B, 35 min 80% B; flow: 0.5 ml/min; temp.: 45° C.; UV detection: 210 nm.

Method 2 (HPLC): Instrument: HP 1050 with variable wavelength detection; column: Chiral AD-H, 250 mm×4.6 mm, 5 µm; Eluent A: n-heptane+0.2% diethylamine, Eluent B: isopropanol+0.2% diethylamine; gradient: 0 min 12.5% B, 30 min 12.5% B; flow: 1 ml/min; temp.: 25° C.; UV detection: 250 nm.

Method 3 (HPLC): Instrument: HP 1050 with variable wavelength detection; column: Chiral AD-H, 250 mm×4.6 mm, 5 µm; Eluent A: n-heptane+0.2% diethylamine, Eluent B: isopropanol+0.2% diethylamine; gradient: 0 min 25% B, 15 min 25% B; flow: 1 ml/min; temp.: 30° C.; UV detection: 250 nm.

EXAMPLES

A) Production of {8-fluoro-2-[4-(3-methoxyphenyl) piperazin-1-yl]-3-[2-methoxy-5-(trifluoromethyl) phenyl]-3,4-dihydroquinazoline-4-yl}acetic acid Example 1A N-(2-fluorophenyl)-N'-[2-methoxy-5-(trifluoromethyl)phenyl]urea

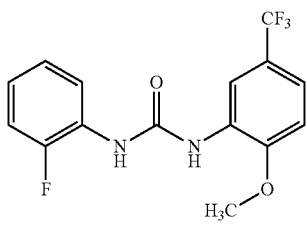 [SMILES: COc1ccc(C(F)(F)F)cc1NC(=O)Nc1ccccc1F]

2-methoxy-5-trifluoromethylphenyl isocyanate (78 kg) is melted at approx. 35° C. and dissolved in acetonitrile (a total of approx. 250 l), then 2-fluoroaniline (39.9 kg) is added and rinsed with acetonitrile (approx. 25 l). The resulting clear solution is agitated for 4 h at reflux and then cooled to approx. 75° C. Once this temperature is reached, the solution is inoculated with seed crystals of the desired end product (200 g), agitated for an additional 15 min., and then cooled to 0° C. over the course of 3 h. The resulting crystalline product is isolated by centrifugation, washed with cold acetonitrile (twice using approx. 13 l), and dried at 45° C. in the VTS under purging with nitrogen (approx. 3.5 h). A total of 101.5 kg of N-(2-fluorophenyl)-N'-[2-methoxy-5-(trifluoromethyl)phenyl]urea is thus obtained as a solid, corresponding to 85.9% of theory.

$^1$H NMR (300 MHz, $d_6$-DMSO): δ=8.93 (s, 1H), 8.84 (s, 1H), 8.52 (d, $^3J$=2.3, 2H), 7.55 (d, $^2J$=7.7, 1H), 7.38-7.26 (m, 3H), 7.22 (d, $^2J$=8.5, 1H), 4.00 (s, 3H) ppm;

MS (API-ES-pos.): m/z=409 [(M+H)$^+$, 100%];

HPLC (Method 1): $R_T$=22.4 and 30.6 min.

Example 2A

Methyl-(2Z)-3-[3-fluoro-2-({[2-methoxy-5-(trifluoromethyl)phenyl]carbamoyl}amino)phenyl]acrylate

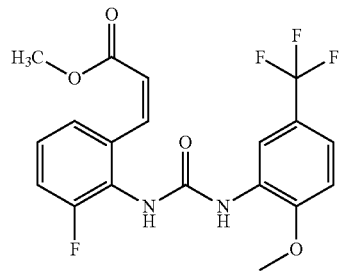 [SMILES: COC(=O)/C=C\c1cccc(F)c1NC(=O)Nc1cc(C(F)(F)F)ccc1OC]

N-(2-fluorophenyl)-N'-[2-methoxy-5-(trifluoromethyl) phenyl] urea (51 kg) is dissolved in acetic acid (approx. 430 l) in one reactor in a nitrogen atmosphere. Methyl acrylate (20.1 kg) is added to the resulting solution and the resulting suspension is agitated until further use. Acetic acid (950 l) is placed in a second reactor, oleum (57 kg) is carefully added and palladium (II) acetate (7 kg) is dissolved in the mixture. The suspension formed in the first reactor is then added to the mixture contained in the second reactor over the course of approx. 2 h; the reaction mixture is overflowed with a mixture of 96% nitrogen and 4% oxygen and the resulting reaction mixture is agitated for approx. 18 h at room temperature. Part of the acetic acid (approx. 900 l) is then distilled off; water (approx. 500 l) is added to the remaining reaction mixture over the course of approx. 1 h and the resulting suspension is agitated for 1 h. The resulting particulate matter is filtered off, washed once with a mixture of acetic acid and water (1:1) and twice with water, and finally dried at approx. 30 mbar and 50° C. A total of 44.8 kg of methyl-(2Z)-3-[3-fluoro-2-({[2-methoxy-5-(trifluoromethyl)phenyl]carbamoyl}amino)phenyl]acrylate is thus obtained as a solid, corresponding to 65.0% of theory.

$^1$H NMR (300 MHz, $d_6$-DMSO): δ=9.16 (s, 1H), 8.84 (s, 1H), 8.45 (d, 1.7 Hz, 1H), 7.73 (m, 2H), 7.33 (m, 3H), 7.22 (d, 8.6 Hz, 1H), 6.70 (d, 16 Hz, 1H), 3.99 (s, 3H), 3.71 (s, 3H) ppm;

MS (API-ES-pos.): m/z=429.9 [(M+NH$_4$)$^+$]; 412.9 [(M+H)$^+$]

HPLC: R$_T$=46.4 min.

Instrument: HP 1100 with variable wavelength detection; column: Phenomenex Prodigy ODS (3) 100A, 150 mm×3 mm, 3 µm; Eluent A: (1.36 g KH$_2$PO$_4$+0.7 ml H$_3$PO$_4$)/l of water, Eluent B: acetonitrile; gradient: 0 min 20% B, 40 min 45% B, 50 min 80% B, 65 min 80% B; flow: 0.5 ml/min; temp.: 55° C.; UV detection: 210 mm.

Example 3A

{8-fluoro-3-[2-methoxy-5-(trifluoromethyl)phenyl]-2-oxo-1,2,3,4-tetrahydroquinazoline-4-yl}methyl acetate

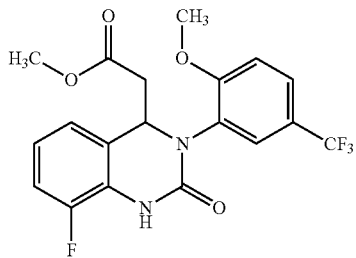 [SMILES: COC(=O)CC1c2cccc(F)c2NC(=O)N1c1cc(C(F)(F)F)ccc1OC]

The compound in Example 2A (75 kg) is suspended in acetone (1600 l), and DBU (5.7 kg) is added. The resulting suspension is heated to reflux and agitated for 4 h at reflux. The resulting solution is cooled to a jacket temperature of 55° C. and filtered through kieselguhr. Part of the solvent (approx. 1125 l) is removed by distillation and the remaining residue is cooled for 2 h to 0° C. The resulting solid is separated by centrifugation, washed twice using cold acetone (approx. 15 l), and dried overnight at 45° C. under reduced pressure and purging with nitrogen to constant mass. A total of 58.3 kg of {8-fluoro-3-[2-methoxy-5-(trifluoromethyl)phenyl]-2-oxo-1,2,3,4-tetrahydroquinazoline-4-yl}methyl acetate is thus obtained as a solid, corresponding to 84.1% of theory.

HPLC (Method 1): R$_T$=19.4 min.

Example 4A (2S,3S)-2,3-bis[(4-methylbenzoyl)oxy]succinic acid-{(4S)-8-fluoro-2-[4-(3-methoxyphenyl)piperazine-1-yl]-3-[2-methoxy-5-(trifluoromethyl)phenyl]-3,4-dihydroquinazoline-4-yl}methyl acetate (1:1 salt) chlorination/amination/crystallization

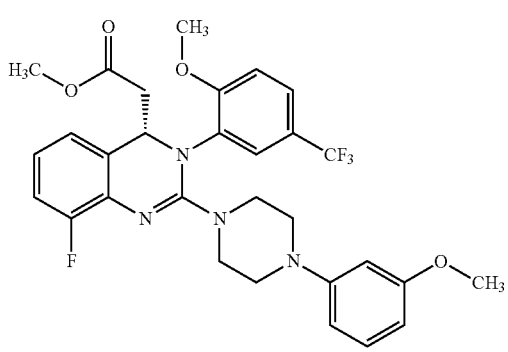

-continued

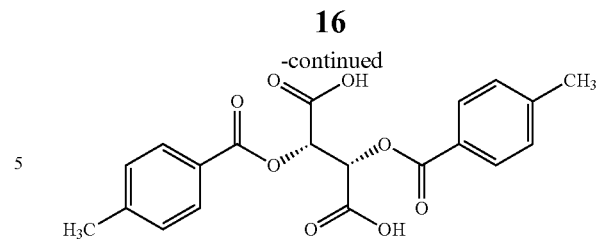

A solution of {8-fluoro-3-[2-methoxy-5-(trifluoromethyl)phenyl]-2-oxo-1,2,3,4-tetrahydroquinazoline-4-yl}methyl acetate (Example 3A, 129.2 kg) in chlorobenzene (800 l) is heated to reflux and azeotropically dried. Phosphorous oxychloride (144 kg) is added, and the reaction mixture is agitated for 3 h at reflux. Next, DBU (95 kg) and chlorobenzene (45 l) are added and agitated for an additional 9 h at reflux. The reaction mixture is cooled to room temperature, hydrolyzed by adding water, diluted with chlorobenzene (80 l), and neutralized with an aqueous solution of ammonia (25%). The phases are separated, the organic phase is washed with water and the solvent is distilled off. The remaining residue is dissolved in dioxane (170 l). 3-methoxyphenylpiperazine (66 kg), DBU (52 kg), and an additional 90 l of dioxane are added and the reaction mixture is heated for 4 h at reflux. The reaction mixture is cooled to room temperature, added to ethyl acetate (1300 l), washed once with water, 3 times with 0.2 N HCl, and once with an aqueous solution of NaCl, and the solvent is distilled off. The resulting residue is dissolved in ethyl acetate (800 l) and added to a solution of (2S,3S)-2,3-bis[(4-methylbenzoyl)oxy]succinic acid (121 kg) in ethyl acetate (600 l). The resulting mixture is agitated for approx. 60 min. at room temperature and then inoculated with (2S,3S)-2,3-bis[(4-methylbenzoyl)oxy]succinic acid-{(4S)-8-fluoro-2-[4-(3-methoxyphenyl)piperazine-1-yl]-3-[2-methoxy-5-(trifluoromethyl)-phenyl]-3,4-dihydroquinazoline-4-yl}methyl acetate and agitated for 3 days at room temperature. It is then cooled to 0-5° C. and agitated for an additional 3 h. The suspension is filtered and the remaining solid is rewashed in batches with ethyl acetate. A total of about 141 kg (calculated as dry weight) of the salt is thus obtained as a solid, corresponding to around 46.2% of theory, in three stages (chlorination, amination and crystallization) compared to the racemate.

$^1$H NMR (300 MHz, d$_6$-DMSO): δ=7.90 (d, $^2$J=7.8, 4H), 7.56 (d, $^2$J=8.3, 1H), 7.40 (d, $^2$J=7.8, 4H), 7.28-7.05 (m, 4H), 6.91-6.86 (m, 2H), 6.45 (d, $^2$J=8.3, 1H), 6.39-6.36 (m, 2H), 5.82 (s, 2H), 4.94 (m, 1H), 4.03 (q, $^2$J=7.1, 2H), 3.83 (brs, 3H), 3.69 (s, 3H), 3.64 (s, 3H), 3.47-3.36 (m, 8H and water, 2H), 2.98-2.81 (m, 5H), 2.58-2.52 (m, 1H), 2.41 (s, 6H), 1.99 (s, 3H), 1.18 (t, $^2$J=7.2, 3H) ppm;

HPLC (Method 1): R$_T$=16.6 and 18.5 min.

Example 5A (2S,3S)-2,3-bis[(4-methylbenzoyl)oxy]succinic acid-{(4S)-8-fluoro-2-[4-(3-methoxyphenyl)piperazine-1-yl]-3-[2-methoxy-5-(trifluoromethyl)phenyl]-3,4-dihydroquinazoline-4-yl}methyl acetate (1:1 salt)/recrystallization (2S,3S)-2,3-bis[(4-methylbenzoyl)oxy]succinic acid-(S){(4S)-8-fluoro-2-[4-(3-methoxyphenyl)piperazine-1-yl]-3-[2-methoxy-5-(trifluoromethyl)phenyl]-3,4-dihydroquinazoline-4-yl}acetic acid methyl ester (1:1 salt) (141 kg, calculated as dry weight) is suspended in ethyl acetate (1400 l) and dissolved by heating to reflux (77° C.). The solution is filtered and slowly cooled to room temperature, which results in spontaneous crystallization. The suspension is agitated for 16 h at RT, and then cooled to 0-5° C. and agitated for an additional 3 h. The suspension is filtered and the remaining solid is rewashed with cold ethyl acetate. The crystals are dried for 16 h in a vacuum at around 40° C. A total of 131.2 kg of the salt is obtained as a solid, corresponding to 93.0% of theory.

HPLC (Method 1): $R_T$=16.9 and 18.8 min.;
HPLC (Method 3): 99.9% e.e.

Example 6A (S)-{8-fluoro-2-[4-(3-methoxyphenyl)piperazine-1-yl]-3-(2-methoxy-5-trifluoromethyl-phenyl)-3,4-dihydroquinazoline-4-yl}acetic acid

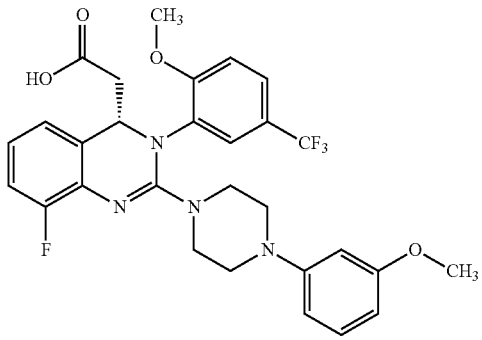 [SMILES: COc1cccc(N2CCN(C3=Nc4c(F)cccc4[C@H](CC(=O)O)N3c3cc(C(F)(F)F)ccc3OC)CC2)c1]

A mixture of (2S,3S)-2,3-bis[(4-methylbenzoyl)oxy]succinic acid-{(4S)-8-fluoro-2-[4-(3-methoxyphenyl)piperazine-1-yl]-3-[2-methoxy-5-(trifluoromethyl)phenyl]-3,4-dihydroquinazoline-4-yl}acetic acid methyl ester (1:1 salt) (30.8 kg), sodium bicarbonate (16.4 kg), and water (315 l) is mixed with MTBE (160 l). The phases are separated and the organic phase is treated with 35 l of an approximately seven-percent aqueous solution of sodium bicarbonate. The phases are separated and the organic phase is added to 125 l of an approximately four-percent aqueous solution of sodium hydroxide. The reaction mixture is heated to reflux, the solution is evaporated to dryness, and the reactor contents are then agitated for an additional 5 h at 55-60° C. The reaction mixture is then added at approx. 22° C. to MTBE (160 l) and water (65 l) and agitated. The phases are separated and the organic phase is extracted with an approximately six-percent aqueous solution of sodium chloride (30 l). The combined aqueous phases are mixed with water (25 l) and MTBE (160 l) and the pH value is adjusted to approx. 6.5 with approx. 1 N of hydrochloric acid. The organic phase is separated, the solvent is evaporated to dryness, and the residue is dissolved in acetone (approx. 75 l). The solvent is changed to acetone (6 distillations with approx. 130 l each). The final product is then precipitated by adding water, isolated through centrifugation, and dried in a vacuum dryer. A total of 16.5 kg of (S)-{8-fluoro-2-[4-(3-methoxyphenyl)piperazine-1-yl]-3-(2-methoxy-5-trifluoromethylphenyl)-3,4-dihydroquinazoline-4-yl}acetic acid is thus obtained as an amorphous solid, corresponding to 96.4% of theory.

$^1$H NMR (300 MHz, $d_6$-DMSO): δ=7.53 (d, $^2$J=8.4, 1H), 7.41 (brs, 1H), 7.22 (d, $^2$J=8.5, 1H), 7.09-7.01 (m, 2H), 6.86 (m, 2H), 6.45 (dd, $^2$J=8.2, $^3$J=1.8, 1H), 6.39-6.34 (m, 2H), 4.87 (t, $^2$J=7.3, 1H), 3.79 (brs, 3H), 3.68 (s, 3H), 3.50-3.38 (m, 4H), 2.96-2.75 (m, 5H), 2.45-2.40 (m, 1H) ppm;

MS (API-ES-neg.): m/z=571 [(M+H), 100%];
HPLC (Method 1): $R_T$=15.1 min;
HPLC (Method 2): 99.8% e.e.; Pd (ICP): <1 ppm.

B) Exemplary Embodiments

Crystallization Experiments

Crystallization experiments to discover a suitable crystalline salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid were carried out for acid salts as well as for base salts. The crystallization experiments were performed, starting from (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid and the respective acid or base, either by slurrification in the respective given solvent for one week at 20° C., or by crystallization by means of cooling/evaporation proceeding from a solution that was kept at 50° C. for 4 hours, followed by slow cooling to 20° C. at a rate of 3° C./hour.

The results for the crystallization experiments with acids or bases are given below in Tables 1 and 2, where the abbreviation API denotes (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid.

"API" is the acronym for "active pharmaceutical ingredient".

TABLE I

| Crystallization experiments using acid counterions | | | | |
|---|---|---|---|---|
| Counter-ions | Ratio API: Counter-ions | Method | Solvent | Result (XRPD) |
| HCl | 1:2 | Cooling | Acetone, Acetonitrile, Methanol, THF | amorphous |
| | | Slurrification | Water, Acetonitrile, Methanol and Ethanol | |
| Citric acid | 1:1 | Cooling | Acetone, Acetonitrile, Methanol, THF | amorphous |
| | | Slurrification | Water, Acetonitrile Methanol and Ethanol | |
| Phosphoric acid | 1:1 | Cooling | Acetone, Acetonitrile, Methanol, THF | amorphous |
| | | Slurrification | Water, Acetonitrile, Methanol and Ethanol | |
| Gluconic acid | 1:1 | Cooling | Acetone, Acetonitrile, Methanol THF | amorphous |
| | | Slurrification | Water, Acetonitrile Methanol and Ethanol | |
| Lactic acid | 1:1 | Cooling | Acetone, Acetonitrile, Methanol THF | amorphous |
| | | Slurrification | Water, Acetonitrile Methanol and Ethanol | |
| Maleic acid | 1:1 | Cooling | Acetone, Acetonitrile, Methanol, THF | amorphous |
| | | Slurrification | Water, Acetonitrile Methanol and Ethanol | |
| Succinic acid | 1:1 | Cooling | Acetone, Acetonitrile, Methanol, THF | amorphous |
| | | Slurrification | Water, Acetonitrile Methanol and Ethanol | |
| Sulfuric acid | 1:1 | Cooling | Acetone, Acetonitrile, Methanol, THF | amorphous |
| | | Slurrification | Water, Acetonitrile Methanol and Ethanol | |
| Tartaric acid | 1:1 | Cooling | Acetone, Acetonitrile, Methanol, THF | amorphous |
| | | Slurrification | Water, Acetonitrile Methanol and Ethanol | |
| Benzoic acid | 1:1 | Cooling | Acetone, Acetonitrile, Methanol, THF | amorphous |

TABLE 1-continued

Crystallization experiments using acid counterions

| Counter-ions | Ratio API: Counter-ions | Method | Solvent | Result (XRPD) |
|---|---|---|---|---|
| | | Slurrification | Water, Acetonitrile Methanol and Ethanol | |
| Fumaric acid | 1:1 | Cooling | Acetone, Acetonitrile, Methanol, THF | amorphous |
| | | Slurrification | Water, Acetonitrile Methanol and Ethanol | |
| Maleic acid | 1:1 | Cooling | Acetone, Acetonitrile, Methanol, THF | amorphous |
| | | Slurrification | Water, Acetonitrile Methanol and Ethanol | |
| Methane-sulfonic acid | 1:1 | Cooling | Acetone, Acetonitrile, Methanol, THF | amorphous |
| | | Slurrification | Water, Acetonitrile Methanol and Ethanol | |

TABLE 2

Crystallization experiments using basic counterions

| Counterions | Method | Solvent | Result |
|---|---|---|---|
| NaOH | Cooling | Acetone + Isopropyl ether 1:1, Acetonitrile + Isopropyl ether 1:1, | crystalline: Methanol, Ethanol |
| | Slurrification | Methanol + Isopropyl ether 1:1, THF and Isopropyl ether 1:1 Water, Acetonitrile, Methanol and Ethanol | amorphous: all others |
| Erbumine | Cooling | Acetone + Isopropyl ether 1:1, Acetonitrile + Isopropyl ether 1:1, | amorphous |
| | Slurrification | Methanol + Isopropyl ether 1:1, THF and Isopropyl ether 1:1 Water, Acetonitrile, Methanol and Ethanol | |
| 2-Amino-2-methyl propanol | Cooling | Acetone + Isopropyl ether 1:1, Acetonitrile + Isopropyl ether 1:1, | amorphous |
| | Slurrification | Methanol + Isopropyl ether 1:1, THF and Isopropyl ether 1:1 Water, Acetonitrile, Methanol and Ethanol | |
| 2-Amino-2-methyl-1,3-propanediol | Cooling | Aceton + Isopropyl ether 1:1, Acetonitrile + Isopropyl ether 1:1, | crystalline: THF, Acetonitrile |
| | Slurrification | Methanol + Isopropyl ether 1:1, THF and Isopropylether 1:1 Water, Acetonitrile, Methanol and Ethanol | amorphous: all others |
| Tromethamine | Cooling | Acetone + Isopropyl ether 1:1, Acetonitrile + Isopropyl ether 1:1, | amorphous |
| | Slurrification | Methanol + Isopropyl ether 1:1, THF and Isopropyl ether 1:1 Water, Acetonitrile, Methanol and Ethanol | |
| Dimethylaminoethanol | Cooling | Acetone + Isopropyl ether 1:1, Acetonitrile + Isopropyl ether 1:1, | amorphous |
| | Slurrification | Methanol + Isopropyl ether 1:1, THF and Isopropyl ether 1:1 Water, Acetonitrile, Methanol and Ethanol | |
| Lysine | Cooling | Acetone + Isopropyl ether 1:1, Acetonitrile + Isopropyl ether 1:1, | amorphous |
| | Slurrification | Methanol + Isopropyl ether 1:1, THF and Isopropylether 1:1 Water, Acetonitrile, Methanol and Ethanol | |
| N-(2-Hydroxyethyl)pyrrolidine | Cooling | Acetone + Isopropyl ether 1:1, Acetonitrile + Isopropyl ether 1:1, | amorphous |
| | Slurrification | Methanol + Isopropyl ether 1:1, THF and Isopropyl ether 1:1 Water, Acetonitrile, Methanol and Ethanol | |

Noticeable with these experiments is that, in general, it has proven extremely difficult to produce crystalline salts of (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid, in particular it is noticeable that crystallization using acid counterions was a complete failure.

Due to the fact that it crystallizes only in organic solvents such as tetrahydrofuran and acetonitrile, which can give rise to undesirable impurities, the 2-amino-2-methyl-1,3-propanediol salt of (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid, tends to be unsuitable for further pharmaceutical development.

In view of the positive results obtained with sodium hydroxide, further crystallization experiments were carried out using alkali metal and/or alkaline earth metal hydroxides under crystallization conditions similar to those used for sodium salt. It was found that further crystalline salts could be obtained only when calcium hydroxide was used.

Example 1

Monosodium salt of {8-fluoro-2-[4-(3-methoxyphenyl)piperazin-1-yl]-3-[2-methoxy-5-(trifluoromethyl)phenyl]-3,4-dihydroquinazoline-4-yl}acetic acid 333.1 g of (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid (Example 6A) are dissolved in 1300 ml of a mixture of ethanol and diisopropyl ether (1:1) in a 2000 ml three-neck flask. 21.9 g (546.84 mmol) of NaOH are added as a solid to the solution. The mixture is heated for 25 min. to an inner temperature of 50° C., and this yields a clear orange-coloured solution. The solution thus obtained is stirred for 3 hours at this temperature, and a thin suspension is formed already after 1 hour. The reaction mixture is then cooled down for 10 hours at a cooling rate of 3° C./hour to an inner temperature of 20° C. and then stirred for a further 5 hours at this temperature. The total volume of the reaction mixture is reduced under vacuum to approximately 750 ml and the suspension obtained in this way is stirred at 20° C. for 2 hours. Next, 250 ml diisopropyl ether is added over a period of 10 min. to the reaction mixture obtained and the mixture is stirred for further 2 hours. The crystalline product which is obtained is vacuumed off by a suction device, washed 2× with in each case 250 ml diisopropyl ether, and dried in a vacuum drying cabinet for 20 hours at 20° C. and 160 mbar. The crystalline solid obtained in this way is then dried for 10 min. at 90° C. in an IR dryer and then again for further 16 hours at 60° C. in the vacuum drying cabinet. In this way a total of 274.4 g (86% of the theoretical yield) of the desired crystalline sodium salt is obtained.

Example 2

Production of the 3-hydrate of the monosodium salt of (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid About 300 mg of the sodium salt from Example 1 are suspended in 1 ml ethanol (containing 4% water) and shaken for a week at 25° C. The solid obtained is filtered off and the residue is dried at room temperature and ambient humidity. The residue obtained corresponds to the title compound as trihydrate.

The residue obtained was examined by X-ray diffractometry. The diffractogram obtained is depicted in FIG. 1.

The X-ray diffractogram was recorded using an XRD transmission/reflection diffractometer X'Pert PRO (PANalytical) at room temperature (radiation: copper, Kα1, wavelength: 1.5406 Å). There was no preparation of the sample.

The peak lists for the salt of Example 2 as well as the salts of Examples 3 and 4 are shown in the following Table 3.

TABLE 3

Peak lists of the powder diffractograms for the salts of Examples 2, 3 and 4
2 Theta

| Example 2 | Example 3 | Example 4 |
|---|---|---|
| 6.2 | 4.6 | 6.0 |
| 9.4 | 6.1 | 6.2 |
| 11.3 | 6.3 | 7.6 |
| 12.4 | 7.6 | 9.6 |
| 12.9 | 8.8 | 9.4 |
| 15.6 | 9.2 | 9.6 |
| 16.4 | 10.6 | 10.7 |
| 16.8 | 11.0 | 11.2 |
| 17.9 | 11.2 | 11.6 |
| 18.6 | 11.6 | 12.1 |
| 18.9 | 12.2 | 12.4 |
| 19.9 | 12.3 | 13.1 |
| 20.9 | 12.6 | 15.1 |
| 21.5 | 12.8 | 15.4 |
| 21.8 | 13.0 | 16.0 |
| 22.4 | 13.3 | 16.1 |
| 22.7 | 13.9 | 16.3 |
| 23.5 | 14.5 | 16.6 |
| 24.9 | 15.3 | 16.9 |
| 25.2 | 15.5 | 17.4 |
| 25.9 | 16.2 | 17.7 |
| 26.4 | 16.3 | 18.2 |
| 26.7 | 16.5 | 18.3 |
| 27.2 | 16.7 | 18.9 |
| 27.4 | 17.0 | 19.2 |
| 28.1 | 17.5 | 19.5 |
| 28.5 | 17.7 | 19.8 |
| 29.5 | 18.1 | 20.0 |
| 30.1 | 18.5 | 20.5 |
| 30.8 | 18.7 | 20.7 |
| 31.2 | 19.4 | 21.3 |
| 32.1 | 19.7 | 21.8 |
| 32.5 | 20.5 | 22.0 |
| 32.8 | 20.8 | 22.4 |
| 33.3 | 21.3 | 22.7 |
| 34.9 | 21.5 | 23.8 |
| 35.6 | 21.7 | 24.2 |
| 36.2 | 22.2 | 24.5 |
| 36.8 | 22.3 | 25.4 |
| 36.8 | 23.0 | 26.2 |
| 37.9 | 23.3 | 26.3 |
| | 23.7 | 26.5 |
| | 24.2 | 27.0 |
| | 24.8 | 27.5 |
| | 25.4 | 28.3 |
| | 25.9 | 29.4 |
| | 26.3 | 31.5 |
| | 26.5 | 34.1 |
| | 26.9 | 35.9 |
| | 27.3 | 37.0 |
| | 27.9 | 37.3 |
| | 28.2 | |
| | 28.7 | |
| | 29.0 | |
| | 29.3 | |
| | 30.5 | |
| | 31.9 | |
| | 32.4 | |
| | 33.1 | |
| | 34.1 | |
| | 34.1 | |
| | 36.0 | |
| | 37.4 | |

Example 3

Production of the 2,5 hydrate of the calcium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid 10 g of (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid (Example 6A) are dissolved in 45 ml of ethanol in a 50 ml three-neck flask and 1.294 g Ca(OH)$_2$ are added as a solid in the form of a powder to the solution obtained. The resulting suspension is heated for 25 min. to 50° C. and then stirred for 3 hours at this temperature. 62.6 g of water are added to the suspension obtained in this way and the resulting solution is cooled to 0° C. Previously produced seed crystals are added to the solution thus obtained and the suspension, which contains a partially oily product, is heated to room temperature and allowed to remain at room temperature for 72 hours. The suspension thus obtained is again cooled to 0° C. and then stirred for 2 h at this temperature. The crystalline product that is obtained is filtered off and washed 2× with in each case 15 ml of a 1:1 mixture of ethanol and water and then dried at 50° C. and 160 mbar in the vacuum drying cabinet. Altogether 7.4 g (68.5% of the theoretical yield) of the salt is obtained as a crystalline solid.

Figure 2:
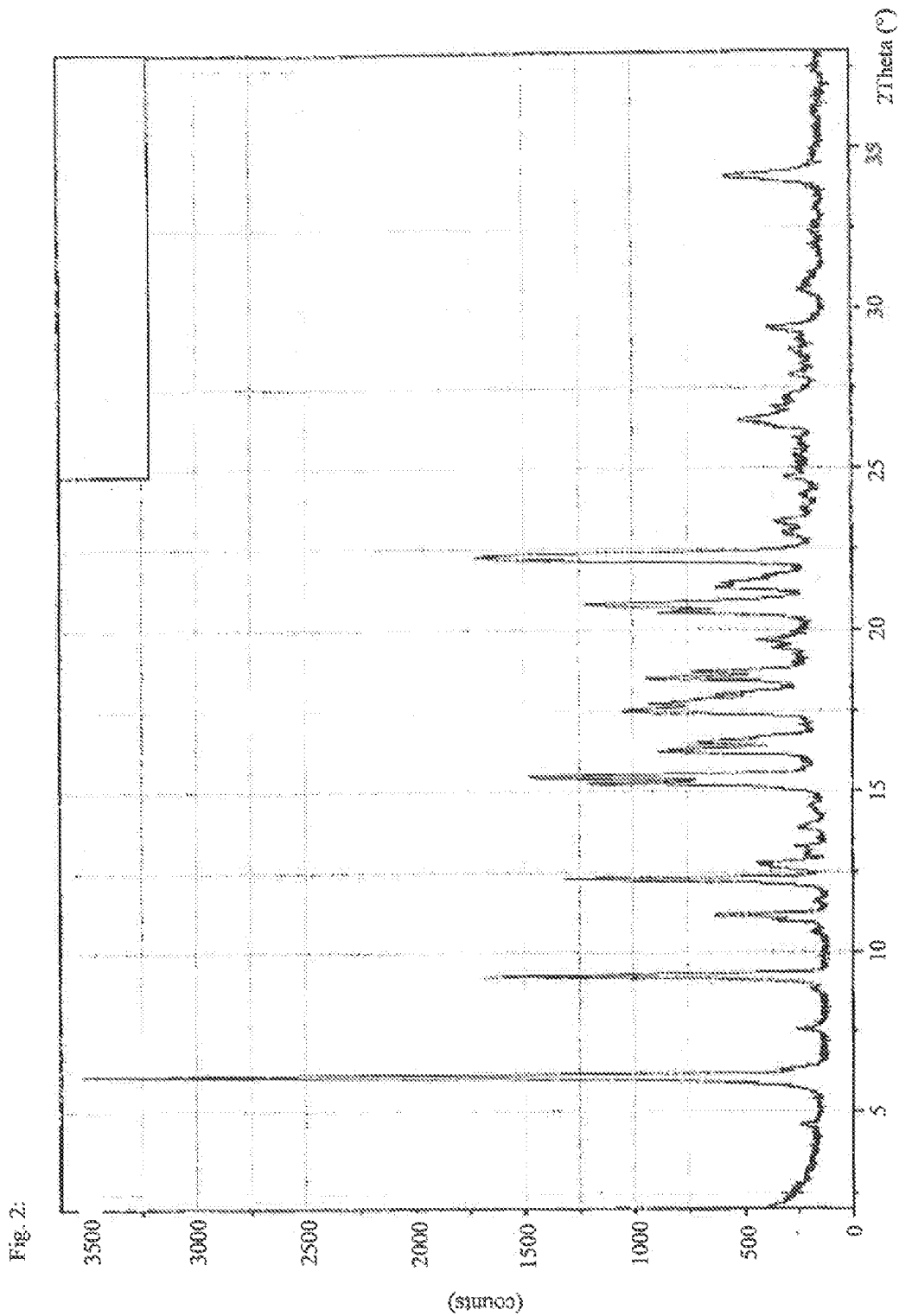
FIG. 2 an X-ray powder diffractogram (XRD) of a 2,5-hydrate of the calcium salt of {8-fluoro-2-[4-(3-methoxyphenyl)piperazine-1-yl]-3-[2-methoxy-5-(trifluoromethyl) phenyl]-3,4-dihydroquinazoline-4-yl}acetic acid that was produced according to Example 3.

Using the crystalline solid obtained in Example 3 an X-ray powder diffractogram (XRD), which is shown in FIG. 2, was recorded under the same conditions as those mentioned in Example 2.

Example 4

3,5-hydrate of the calcium salt of (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid About 100 mg of the salt obtained in Example 3 are suspended in 1 ml of ethanol and water (1:1) and the suspension obtained is shaken for 1 week at 25° C. The crystallized solid obtained is filtered off and the residue obtained is dried at room temperature and ambient humidity. The residue obtained corresponds to the 3,5-hydrate of the calcium salt of (S)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid.

Figure 3:
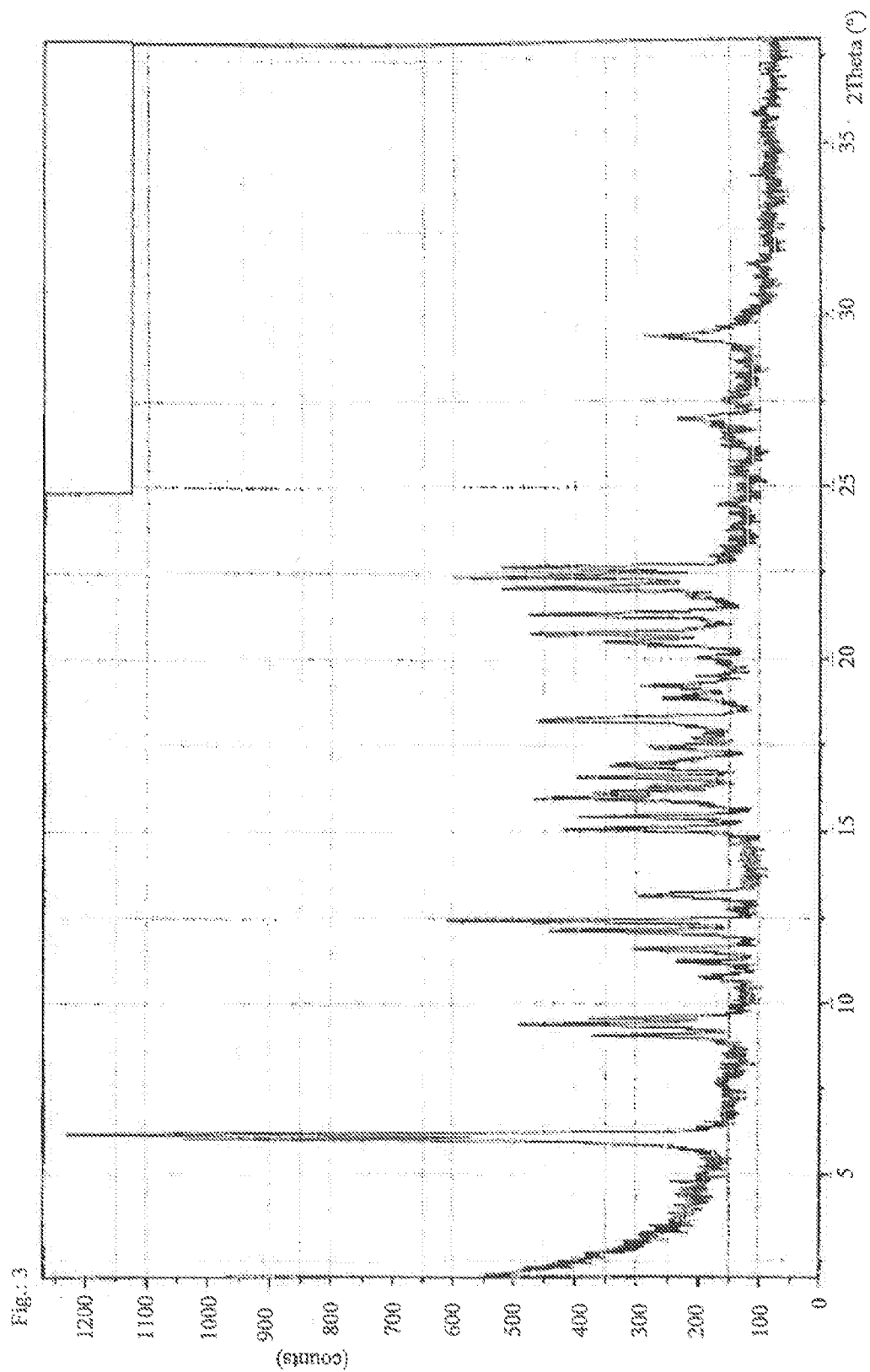
FIG. 3 an X-ray powder diffractogram (XRD) of a 3,5-hydrate of the calcium salt of {8-fluoro-2-[4-(3-methoxyphenyl)piperazine-1-yl]-3-[2-methoxy-5-(trifluoromethyl) phenyl]-3,4-dihydroquinazoline-4-yl}acetic acid that was produced according to Example 4.

Using the crystalline solid obtained in Example 4, an X-ray powder diffractogram (XRD), which is shown in FIG. 3, was recorded under the same conditions as those mentioned in Example 2.

C) Solubility Measurements

In order to determine the solubility, a saturated solution of the salt from Example 2 was prepared in phosphate buffer at pH 7.0 and shaken at room temperature for 2 hours. The suspensions obtained were filtered by means of a syringe filter (0.45 μm pore diameter) and after being diluted the clear solutions were measured by HPLC. Pure phosphate buffer was used as the blank sample. The solubility was calculated in terms of the absorption of a reference solution of the amorphous zwitterion in phosphate buffer. The results of the measurement are shown below in Table 4.

TABLE 4

| Compound | Solubility in buffer [mg/ml] |
|---|---|
| Example 6a | 0.4 (at pH 7) |
| Example 2 | >91.7 |

D) Assessment of Physiological Efficacy

The in vitro effects of the compositions according to the present invention on the replication of the HCMV (human cytomegalovirus) can be seen in the following antiviral assay:

HCMV Fluorescence-Reduction Test.

The test compositions are used as a 50-millimolar (mM) solution in dimethyl sulphoxide (DMSO). Ganciclovir®, Foscarnet® or Cidofovir® can be used as reference compositions. One day before the beginning of the test, 1.5×10$^4$ human foreskin fibroblasts (NHDF cells)/well are seeded in 200 μl of cell culture medium in Wells B2-G11 of 96-well plates (black with transparent floor). The wells along the edges of each 96-well plate are filled with 200 μl of medium only in order to prevent edge effects. On the day of the test the cell culture medium in Wells B2-G11 of each 96-well plate is vacuumed off by a suction device and replaced with 100 μl of virus suspension (multiplicity of infection (MOI): 0.1-0.2). The virus used is a recombinant HCMV which has integrated an expression cassette for green fluorescence protein (GFP) in the virus genome (HCMV AD 169 RV-HG [E. M. Borst, K. Wagner, A. Binz, B. Sodeik, and M. Messerle, 2008, J. Virol. 82:2065-2078.]). After an incubation time of 2 h at 37° C. and 5% CO$_2$, the virus inoculate is vacuumed off by a suction device and all wells, with the exception of the wells in Column 3, are filled with 200 μl of cell culture medium. Column 2 is not treated further and serves as a virus control. The wells in Column 3 are each filled with 300 μl of test substance (diluted in cell culture medium) for duplicate analysis. The concentration of the respective antiviral substance in Column 3 is ~27 times as concentrated as the respective anticipated EC$_{50}$ value. The test substance in Column 3 is diluted in 8 steps to a concentration of 1:3 across the 96-well plate by transferring 100 μL from each column into its respective right-hand column, where it is mixed with the 200 μl of cell culture medium already present there. In this way, three antiviral substances are tested in duplicate analyses. The plates are incubated for 7 days at 37° C. and 5% CO$_2$. Subsequently, all wells on the plate are washed 3 times with PBS (phosphate-buffered saline) and filled with 50 μl of PBS. The GFP intensity of each well in a 96-well plate is then determined using a fluorescence scanner (FluoBox; Bayer Technology Services GmbH; filter settings: GFP, Ex 280 nm, Em 520 nm). The measured values thus obtained can be used to determine the EC$_{50}$ of an anti-HCMV:

EC$_{50}$ (GFP-RA)=substance concentration in μM which reduces GFP fluorescence by 50% in comparison to the untreated virus control.

Representative in vitro efficacy data for the compositions according to the present invention are reproduced in Table 5:

TABLE 5

| Virus strain | Example 6A EC$_{50}$ [μM] | Example 2 EC$_{50}$ [μM] | Ganciclovir EC$_{50}$ [μM] |
|---|---|---|---|
| AD169 RV-HG | 0.0034 | 0.0039 | 2.2 |

E) Pharmaceutical Compositions

Compounds according to the invention can be converted as follows into pharmaceutical composition:

Intravenous Solution:

To produce a first stock solution, 1.0 g of the salt from Example 2 is dissolved in 10 ml of water for injection purposes and the salt is agitated until a clear solution is obtained. This solution is slowly added to a 20 mM phosphate buffer solution in order to produce solutions for intravenous administration with concentrations of 5 mg/ml or 10 mg/ml. The pH values of the respective solutions were at approx. pH 7.6 (5 mg/ml) and approx. pH 7.7 (10 mg/ml). Finally, the solutions obtained are sterile-filtered and filled into appropriate sterilized containers. The containers are sealed with infusion plugs and flange caps.

If necessary, the solutions produced in this way can be lyophilized for storage before the containers are sealed and they can be reconstituted at a later date in order to be used.

Tablet:

In order to produce a solid formulation for oral administration the salt (50%) from Example 2 is screened and mixed with calcium hydrogen phosphate dihydrate (48%), croscarmellose sodium (5%), polyvinylpyrrolidone (5%) and colloidal silica gel (1%). Then, screened magnesium stearate (1%) is added. This press mixture is then directly used to produce tablets.

F) Purity

S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid sodium salt Implementation 313.1 g of S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid were put into a 2000 ml plane ground joint flask. Then a 1300 ml mixture of EtOH (denatured)/diisopropyl ether (1:1) as well as 21.9 g of NaOH pellets were added. By controlling the inner temperature the mixture was heated to an inner temperature of 50° C. (Tm=51° C.) for 25 minutes. The NaOH pellets dissolve, giving a clear orange-coloured solution. The mixture was then stirred for three hours and a suspensions was obtained. Within the next 10 hours the mixture was cooled down at a cooling rate of 3° C. per hour to an inner temperature of approx. 20° C. and then stirred for further five hours at this temperature. This yields a thicker suspension with a total volume of 1500 ml in a plane ground joint flask, and 400 ml of said total volume is crystal volume. Under vacuum the total volume is reduced to approx. 750 ml at 110 to 90 mbar; inner temperature 17-25° C., jacket temperature 35-50° c., distillate 273 g. This was then stirred for about two hours. Within a period of 10 minutes 250 ml diisopropyl ether are added and then stirring is carried out for two hours. The product obtained in this way is isolated and washed twice with in each case 250 ml of diisopropyl ether; wet yield: 284.8 g. The product obtained was dried for 20 hours in the vacuum drying cabinet at 50° C. while purging with nitrogen at approx. 160 mbar; final weight 279.4 g. This product underwent the following analysis:

Analysis

Determination of the Sodium Content

Usually an excess of $HNO_3$ is added to 200 mg of the test substance (S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid sodium salt) and microwave-supported pressure digestion is carried out (according to Method 2011-0606601 Currenta, Leverkusen). The solution is examined for its sodium content using flame atomic absorption spectroscopy (according to Method 2011-0267201 Currenta, Leverkusen).

Result: S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid sodium salt: 3.5 wt. % sodium Modification X-Ray: crystalline Determination of residual solvent: 0.03 wt. % diisopropyl ether HPLC-Analysis Examination of the following specific and non-specific contaminations of S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid sodium salt:

Quinazolyl-piperazine
Di-p-toluoyl tartaric acid
Quinazolyl dipiperazine
Quinazoline ethyl ester
individual non-specific contaminants by means of high-pressure liquid chromatograph (HPLC); Reversed-Phase Method;

Detection: UV-range;

Analysis: Surface percent method with surface correction factors

Equipment

1. High-pressure liquid chromatograph with thermostatically controlled column oven, UV detector and data evaluation system
2. Metal column made of stainless steel
   Length: 15 cm
   Internal diameter: 3.0 mm
   Packing: Prodigy ODS III, 3 μm Reagents 1. Acetonitrile, for the HPLC
2. Potassium dihydrogen phosphate, p.a.
3. o-phosphoric acid 85% strength, p.a.

Test Solution ca. 22 mg sample of S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid sodium salt; accurately weighed, dissolved in acetonitrile, and filled up to 50.0 ml.

Calibration Solution ca. 22 mg reference standard of (S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid, accurately weighed, dissolved in acetonitrile, and filled up to 50.0 ml.

Comparative Solution

A comparative solution, similar to the calibration solution, is prepared. It contains, in addition, a small amount of the organic contaminants (quinazolyl piperazine, di-p-toluoyl tartaric acid, quinazolyl dipiperazine, quinazoline methyl ester).

HPLC-Conditions

The stated conditions are intended as guideline values and, if necessary, in order to achieve optimal separations, they can be adapted to the technical capabilities of the chromatograph and to the properties of the respective column.

Eluents
A. Dissolve 1.36 g potassium dihydrogen phosphate and 0.7 ml o-phosphoric acid 85% strength with water and filled up to 1000.0 ml
B. Acetonitrile
Flow Rate
0.5 ml/min
Temperature of the Column Oven
55° C.
Detection
Measurement wavelength: 210 nm
Bandwidth: 4 nm
Injection Volume
3 µl
Equilibration Time
10 min (under start-up conditions)

| Gradient | | |
|---|---|---|
| Zeit | % A | % B |
| 0.00 | 80 | 20 |
| 40.00 | 55 | 45 |
| 50.00 | 20 | 80 |
| 65.00 | 20 | 80 |

[Translation key:
Zeit=time]
Run Time of the Chromatogram
65 min
Precision
The relative standard deviation of the areas obtained from 6 injections of the reference standard must be ≤1.5%.
Implementation
Chromatograph the test solution, calibration solution and comparative solution under the given conditions.

|  | RT ([min] | RRT | RF |
|---|---|---|---|
| BAY 73-6327 | ca. 27.9 | 1.00 | 1.00 |
| Di-p-toluoylweinsäure | ca. 30.5 | 1.09 | 1.94 |
| Chinazolylpiperazin | ca. 34.4 | 1.24 | 1.02 |
| Chinazolinethylester | ca. 36.1 | 1.37 | 1.05 |
| Chinazolyldipiperazin | ca. 42.9 | 1.54 | 0.81 |

Figure 4:
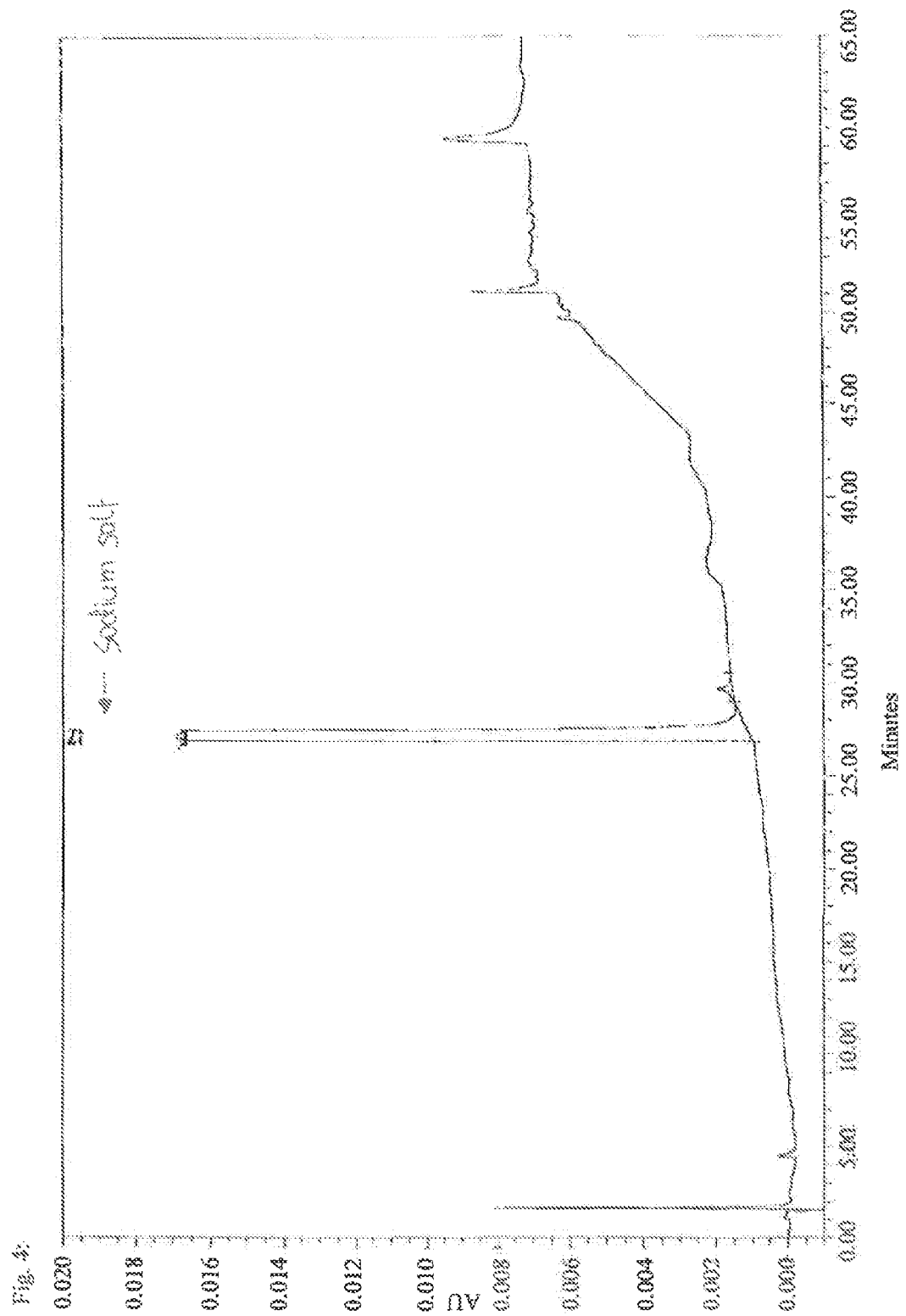
FIG. 4 An HPLC chromatogram for S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid sodium salt.

[Translation key:
Weinsäure=tartaric acid]
Evaluation
Electronic integration of the peak areas.
Calculation of the Content of Organic Impurities (HPLC)
Area percent method with area correction factors (RF), if present.
Result S(+)-{8-fluoro-2-[4-(3-methoxyphenyl)piperazine-1-yl]-3-[2-methoxy-5-(trifluoromethyl)phenyl]-3,4-dihydroquinazoline-4-yl}acetic acid sodium salt:

99.9 area percent
0.0 area percent for known organic contaminants
0.07 area percent for the largest non-specific contaminants
0.0907 area percent for the largest individual non-specific secondary components
88.0 wt. %
For the HPLC-chromatogram and the analysis thereof see FIGS. 4 and 5.

The invention claimed is:

1. A salt of {8-fluoro-2-[4-(3-methoxyphenyl)piperazine-1-yl]-3-[2-methoxy-5 (trifluoromethyl) phenyl]-3,4-dihydroquinazoline-4-yl}acetic acid or a solvate thereof selected from the group consisting of crystalline sodium salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, crystalline calcium salts of {8-fluoro-2-[4-(3-methoxyphenyl)piperazine-1-yl]-3-[2-methoxy-5-(trifluoromethyl)phenyl]-3,4-dihydroquinazoline-4-yl}acetic acid and solvates thereof.

2. The salt according to claim 1, which is the monocalcium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid or a solvate thereof.

3. The salt according to claim 2, which is the 2.5-hydrate of the monocalcium salt of {8-fluoro-2-[4-(3-methoxyphenyl)piperazine- 1-yl]-3-[2-methoxy-5-(trifluoromethyl)phenyl]-3,4-dihydroquinazoline-4-yl}acetic acid.

4. The salt according to claim 3, which shows X-ray powder diffractogram characteristic peaks at about 6.1, 9.2 and 15.5 degrees 2theta.

5. The salt according to claim 2, which is the 3.5-hydrate of the monocalcium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid.

6. The salt according to claim 5, which shows X-ray powder diffractogram characteristic peaks at about 6.2, 12.4 and 22.4 degrees 2theta.

7. The salt according to claim 1, which is the monosodium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid or a solvate thereof.

8. The salt according to claim 7, which is the 3-hydrate of the monosodium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid.

9. The salt according to claim 8, which shows X-ray powder diffractogram characteristic peaks at about 6.2, 20.9 and 22.4 degrees 2theta.

10. A pharmaceutical composition containing a salt according to claim 1 in combination with at least one pharmaceutically acceptable excipient.

11. A process for preparing a salt according to claim 1, comprising the following steps:
   a) dissolving {8-fluoro-2-[4-(3-methoxyphenyl)piperazine-1-yl]-3-[2-methoxy-5-(trifluoromethyl)phenyl]-3,4-dihydroquinazoline-4-yl}acetic acid or a solvate thereof in a mixture of at least one ($C_1$-$C_4$) dialkyl ether and at least one ($C_1$-$C_4$) alcohol, optionally under heat,
   b) adding NaOH or $Ca(OH)_2$ to the solution obtained in step a),
   c) removing a portion of the solvent from the solution obtained in step b) and inoculate, optionally with seed crystals in order to initiate the crystallization of the salt or of a solvate of a salt,
   d) separating the crystallized-out salt or solvate thereof obtained in step c),
   e) optionally stirring the salt or solvate obtained in step d) in a solvent in order to obtain a solvate, and
   f) drying the salt or solvate obtained in step d) or e).

12. The process according to claim 11, wherein the solvent in step e) is a mixture of water and at least one ($C_1$-$C_4$) alcohol.

13. A method for the treatment and/or prophylaxis of a virus infection, comprising administering an effective amount of a salt according to claim 1 to a human or an animal who or which is in need of such a treatment.

14. A method for the treatment of a virus infection, comprising administering an effective amount of a salt according to claim 1 to a human or an animal who or which is in need of such a treatment.

15. The method according to claim 13, wherein the virus infection is by a member of the herpes viridae group of viruses.

16. The method according to claim 13, wherein the virus infection is by human cytomegalovirus.

17. The method according to claim 16, wherein the 2.5-hydrate of the monocalcium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, the 3.5-hydrate of the monocalcium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid or the 3-hydrate of the monosodium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid is administered.

18. The method according to claim 14, wherein the virus infection is by a member of the herpes viridae group of viruses.

19. The method according to claim 14, wherein the virus infection is by human cytomegalovirus.

20. The method according to claim 19, wherein the 2.5-hydrate of the monocalcium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid, the 3.5-hydrate of the monocalcium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid or the 3-hydrate of the monosodium salt of {8-fluoro-2-[4-(3-methoxyphenyl)piperazine-1-yl]-3-[2-methoxy-5-(trifluoromethyl)phenyl]-3,4-dihydroquinazoline-4-yl}acetic acid is administered.

\* \* \* \* \*